United States Patent
Iwanaga et al.

(10) Patent No.: US 8,873,849 B2
(45) Date of Patent: Oct. 28, 2014

(54) IMAGE PROCESSING METHOD, IMAGE DISPLAY METHOD, IMAGE PROCESSING APPARATUS AND A NON-TRANSITORY COMPUTER-READABLE RECORDING MEDIUM

(75) Inventors: Shuji Iwanaga, Koshi (JP); Shinobu Miyazaki, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 182 days.

(21) Appl. No.: 13/524,085

(22) Filed: Jun. 15, 2012

(65) Prior Publication Data
US 2012/0328194 A1    Dec. 27, 2012

(30) Foreign Application Priority Data

Jun. 24, 2011  (JP) .................................. 2011-141128
May 30, 2012  (JP) .................................. 2012-123198

(51) Int. Cl.
*G06K 9/00*  (2006.01)
*G01N 21/95*  (2006.01)
*G06T 5/00*  (2006.01)

(52) U.S. Cl.
CPC ............ *G06T 5/009* (2013.01); *G01N 21/9501* (2013.01); *G06T 2207/30148* (2013.01)
USPC ........... 382/168; 382/164; 382/165; 382/170; 358/518; 358/521

(58) Field of Classification Search
USPC .......... 382/164, 165, 167, 170, 171; 358/518, 358/519, 521
See application file for complete search history.

(56) References Cited

U.S. PATENT DOCUMENTS

| | | | | |
|---|---|---|---|---|
| 7,020,350 B2* | 3/2006 | Sakai et al. | ................... | 382/294 |
| 7,127,098 B2* | 10/2006 | Shimoda et al. | .............. | 382/145 |
| 7,333,677 B2* | 2/2008 | Sakai et al. | ................... | 382/294 |
| 7,505,149 B2* | 3/2009 | Ishiba et al. | .................. | 356/612 |
| 7,821,571 B2* | 10/2010 | Kitagata et al. | ............... | 348/367 |
| 8,035,853 B2* | 10/2011 | Sambongi et al. | ............. | 358/1.9 |
| 8,064,665 B2* | 11/2011 | Couwenhoven et al. | ..... | 382/128 |
| 8,351,698 B2* | 1/2013 | Furuya | .......................... | 382/168 |
| 8,355,595 B2* | 1/2013 | Bressan | ........................ | 382/274 |
| 8,385,680 B2* | 2/2013 | Tada | ............................. | 382/274 |
| 8,625,095 B2* | 1/2014 | Lee et al. | ...................... | 356/364 |

FOREIGN PATENT DOCUMENTS

JP    A-2009-216515    9/2009

* cited by examiner

*Primary Examiner* — Yosef Kassa
(74) *Attorney, Agent, or Firm* — Posz Law Group, PLC

(57) ABSTRACT

An image processing method of picking up an image of a substrate and converting pixel values of the picked-up substrate image makes the pixel values of the picked-up substrate image into a histogram, and creates a tone curve T composed of a periodic function of a predetermined amplitude and a predetermined period based on a distribution of the pixel values in the histogram. The pixel values of the picked-up substrate image are converted using the tone curve T to obtain a substrate image with a high contrast.

16 Claims, 14 Drawing Sheets

FIG.18
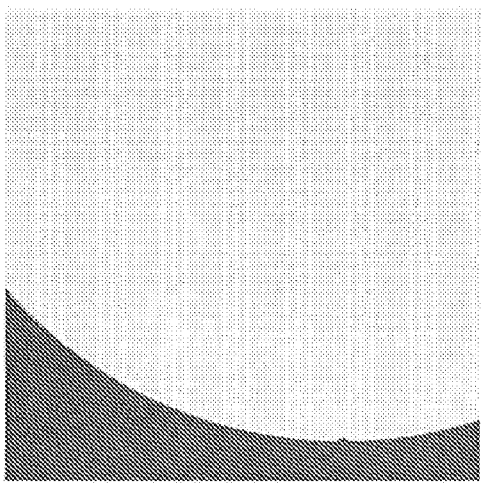
BEFORE IMAGE PROCESSING
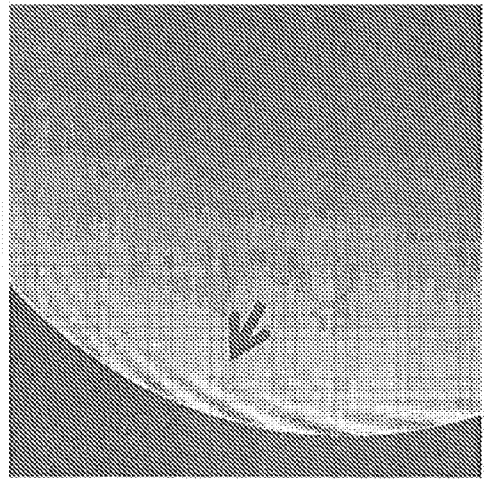
AFTER IMAGE PROCESSING
FIG.19
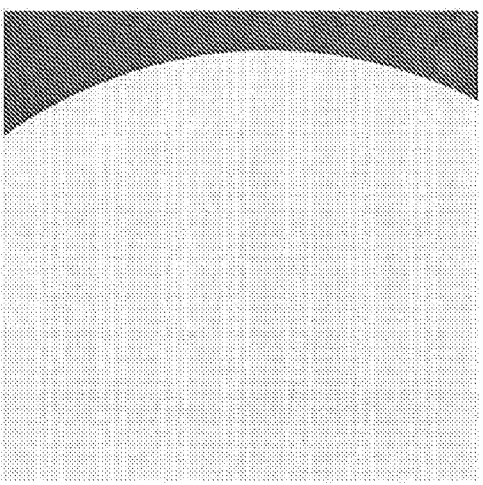
BEFORE IMAGE PROCESSING
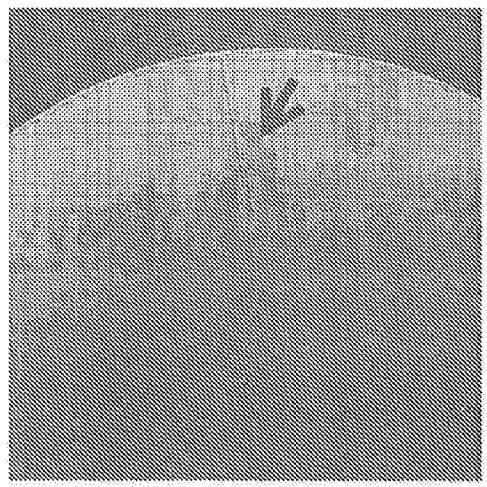
AFTER IMAGE PROCESSING FIG.20
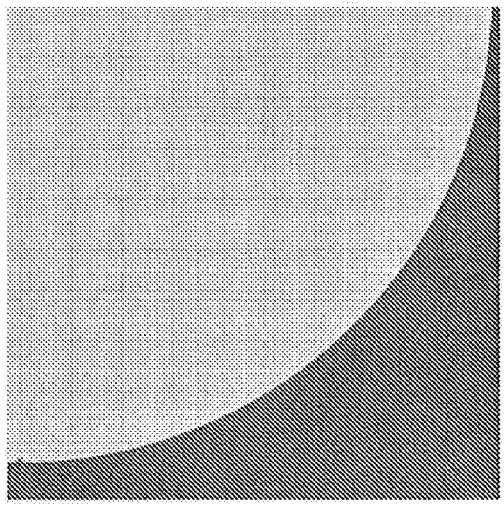
BEFORE IMAGE PROCESSING
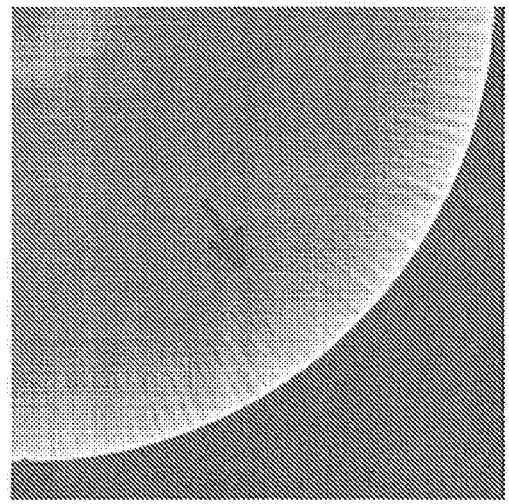
AFTER IMAGE PROCESSING
FIG.21
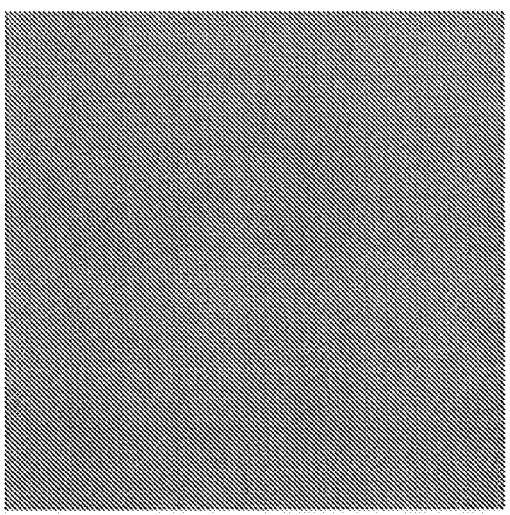
BEFORE IMAGE PROCESSING
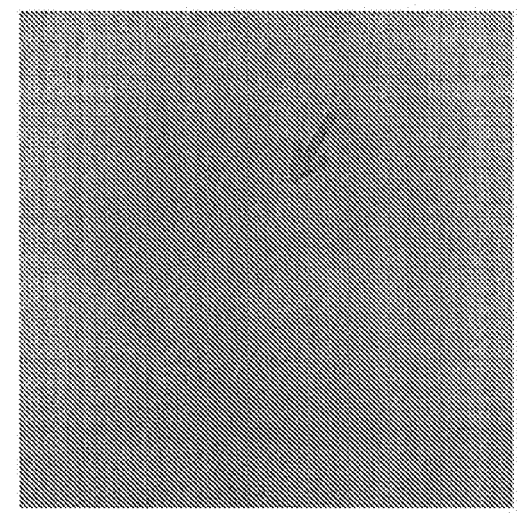
AFTER IMAGE PROCESSING FIG.22
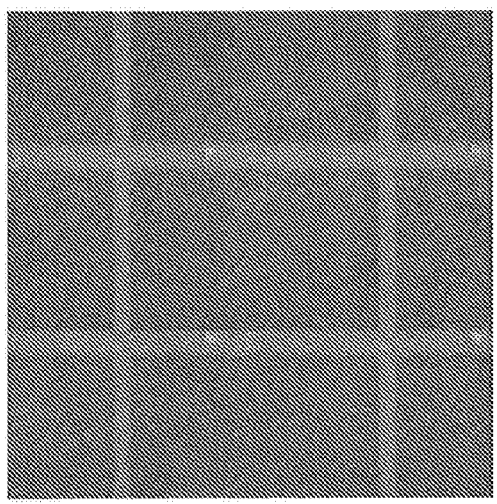
BEFORE IMAGE PROCESSING
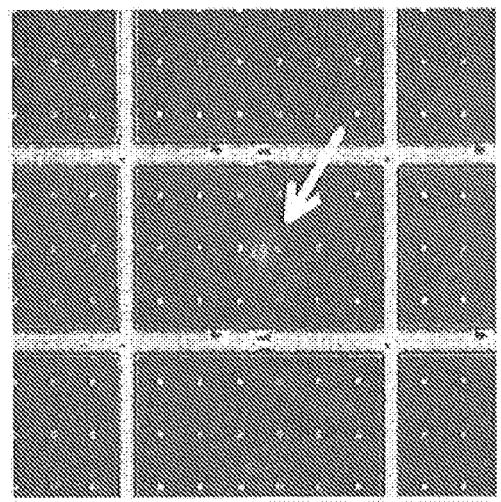
AFTER IMAGE PROCESSING
FIG.23
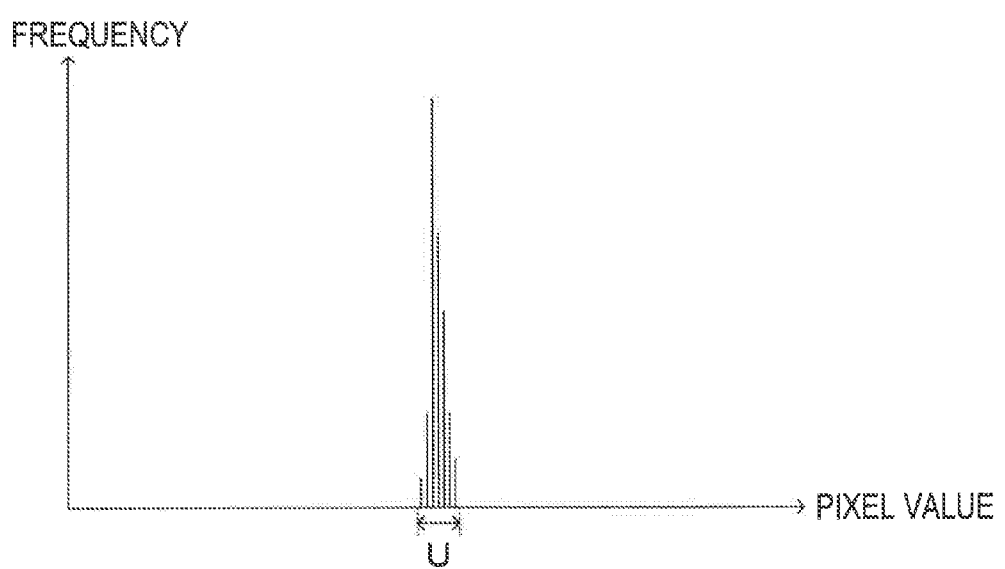

IMAGE PROCESSING METHOD, IMAGE DISPLAY METHOD, IMAGE PROCESSING APPARATUS AND A NON-TRANSITORY COMPUTER-READABLE RECORDING MEDIUM

BACKGROUND OF THE INVENTION

1. Field of the Invention

The present invention relates to an image processing method of converting gradation information on an image of a substrate picked up in an inspection apparatus, and to an image display method, an image processing apparatus, and a computer storage medium.

2. Description of the Related Art

In a photolithography process in manufacturing process of a semiconductor device, for example, a series of treatments such as a resist coating treatment of applying a resist solution onto a wafer to form a resist film, exposure processing of exposing the resist film into a predetermined pattern, a developing treatment of developing the exposed resist film and so on are performed in sequence to form a predetermined resist pattern on the wafer. A series of these treatments are performed in a coating and developing treatment system being a substrate treatment system in which various treatment units treating the wafer treating the wafer, transfer mechanisms transferring the wafer and so on are installed.

The wafer for which a series of photolithography treatments have been performed in the coating and developing treatment system is subjected to a so-called macro defect inspection by a defect inspection apparatus, as to whether or not a predetermined resist film has been formed on the front surface of the wafer, or whether or not there is a scratch or adherence of foreign substance.

In such a macro defect inspection, while a mounting table on which the wafer is mounted is being moved, illumination is applied to the wafer on the mounting table and, for example, an imaging device of a CCD line sensor picks up an image of the front surface of the wafer. Then, the presence or absence of defects on the front surface of the wafer is determined based on the picked-up image. In this event, if the luminance (pixel value) of the picked-up image is too high or too low, the defects on the wafer cannot be determined in some cases. Therefore, to bring the luminance of the image of the wafer to an optimal luminance for defect determination, the illuminance of the illumination illuminating the wafer is adjusted (Patent Document 1).

Patent Document 1: Japanese Laid-open Patent Publication No. 2009-216515

SUMMARY OF THE INVENTION

Incidentally, the image picked up by the above-described imaging device is generally an image of 8 bits (256 gradations). However, the contrast is low in the 8-bit image and causes a problem in which though defects actually occur due to an abnormal film thickness and the like with miniaturization of the semiconductor device in recent years, the defects cannot be recognized. In this case, an operator visually determines the presence or absence of the defects, and it is extremely difficult to judge the presence or absence of the defects even by the visual check of the image when the contrast is low.

As means for emphasizing the contrast in an image having a smaller number of bits, a method of deforming the tone curve is used in some cases. Concretely; the tone curve is deformed so that its slope becomes steep in a region U near the mode value taking the mode value in the histogram as a median value, for example, in the image having the distribution as illustrated in FIG. 23. In other words, the tone curve is deformed to make the interval between the maximum pixel value and the minimum pixel value smaller. In this case, a tone curve T after deformation takes a shape having a steep slope near the mode value, for example, as illustrated in FIG. 24 with the input pixel value (pixel value before conversion) plotted on the horizontal axis and the output pixel value (pixel value after conversion) plotted on the vertical axis. By deforming the tone curve T as described above, the contrast in the region U illustrated in FIG. 23 can be emphasized.

However, when the tone curve is deformed as in FIG. 24, the slope of the tone curve T becomes zero or extremely small in a region outside the region U. Accordingly, the contrast remarkably decreases or the contrast comes into a state of zero in the region outside the region U. In this case, in the image in which the distribution of the pixel values in the histogram has a peak value appearing also in another region V outside the region U, for example, as illustrated in FIG. 25, the pixel values existing in the region V are not displayed on the image or have an extremely low contrast even if they are displayed. Therefore, the presence or absence of defects represented by the pixel values in the region V cannot be judged by the above-described tone curve T.

To emphasize the contrast in the region V, it is necessary to convert the pixel values in the region U using the tone curve T illustrated in FIG. 24 and then deform again the tone curve T to cope with the region V. However, in such a case, an operation of deforming the tone curve T is required every time, resulting in a decreased throughput of the defect inspection. Further, since the images of the region U and the region V cannot be displayed on one image at the same time, the contents of the defects cannot be accurately grasped in some cases.

On the other hand, it is conceivable to use a high dynamic range camera system for the imaging device as the method of obtaining an image with a high contrast. However, such an imaging device leads to an increased cost. Further, browsing the image in the high dynamic range cannot be handled with generally used image display software, and exclusive software needs to be used. This also leads to an increase in cost and a decrease in general versatility.

The present invention has been made in consideration of the point, and its object is to increase the contrast of an image picked up by an imaging device to improve the visibility thereof.

To achieve the above object, the present invention is an image processing method of picking up an image of a substrate and converting pixel values of the picked-up substrate image, including the steps of: making the pixel values of the picked-up substrate image into a histogram; creating a tone curve composed of a periodic function of a predetermined amplitude and a predetermined period based on a distribution of the pixel values in the histogram; and converting the pixel values of the picked-up substrate image using the tone curve.

According to the present invention, since the tone curve composed of the periodic function is used for converting the pixel values of the substrate image, the slope of the tone curve can be made steep in the whole region of the histogram. Accordingly, performing the image processing using the tone curve makes it possible to create an image with a high contrast from the image picked up using the imaging device with a smaller number of bits. This enables improvement in visibility of the image and resultantly performance of a defect inspection with a high accuracy. Further, since the tone curve is the periodic function in which the maximum value and the minimum value are periodically repeated, an image with a high contrast can be obtained also from the pixel values existing in the above-described region V. Furthermore, because of use of the periodic function, the contrast of the image can be easily adjusted by changing the phase and the period of the periodic function.

The periodic function may be a trigonometric function or may be made by combining a plurality of trigonometric functions. In this case, each of the plurality of trigonometric functions may be obtained correspondingly to each of a plurality of peaks of the pixel values existing in the histogram. Further, a shape of the tone curve may be a saw-tooth wave shape.

The trigonometric function may be obtained by an expression expressed by $$Y=\{(2^C/2)-N\}\times[\sin\{(X-A)/B\}+1].$$

In this case, Y is a pixel value after conversion, C is a number of bits of the substrate image, N is a positive constant equal to or larger than ½, X is a pixel value of the picked-up substrate image, A is a phase, and B is a period. In this case, A in the trigonometric function may be a mode value of the pixel values in the histogram.

According to the present invention in another aspect, there is provided a program running on a computer of a control unit controlling a substrate treatment system to cause the substrate treatment system to perform the image processing method.

According to the present invention in still another aspect, there is provided a computer-readable storage medium having the program stored therein.

The present invention according to yet another aspect is an image processing apparatus converting pixel values of a substrate image picked up by an imaging device, including: a calculation part making pixel values of the picked-up substrate image into a histogram; an arithmetic part creating a tone curve composed of a periodic function of a predetermined amplitude and a predetermined period based on a distribution of the pixel values in the histogram; and a conversion part converting the pixel values of the picked-up substrate image using the tone curve.

The periodic function may be a trigonometric function or may be made by combining a plurality of trigonometric functions. In this case, each of the plurality of trigonometric functions may be obtained correspondingly to each of a plurality of peaks of the pixel values existing in the histogram. Further, a shape of the tone curve may be a sawtooth wave shape.

The trigonometric function may be obtained by an expression expressed by $$Y=\{(2^C/2)-N\}\times[\sin\{(X-A)/B\}+1].$$

In this case, Y is a pixel value after conversion, C is a number of bits of the substrate image, N is a positive constant equal to or larger than ½, X is a pixel value of the picked-up substrate image, A is a phase, and B is a period. In this case, A in the trigonometric function may be a mode value of the pixel values in the histogram.

According to the present invention, it is possible to increase the contrast of an image picked up by an imaging device to improve the visibility thereof.

BRIEF DESCRIPTION OF THE DRAWINGS

FIG. 18 shows images before the image processing and after the image processing;

FIG. 19 shows images before the image processing and after the image processing;

FIG. 20 shows images before the image processing and after the image processing;

FIG. 21 shows images before the image processing and after the image processing;

FIG. 22 shows images before the image processing and after the image processing;

FIG. 23 is a histogram of a substrate image;

DETAILED DESCRIPTION OF THE INVENTION

Figure 1:
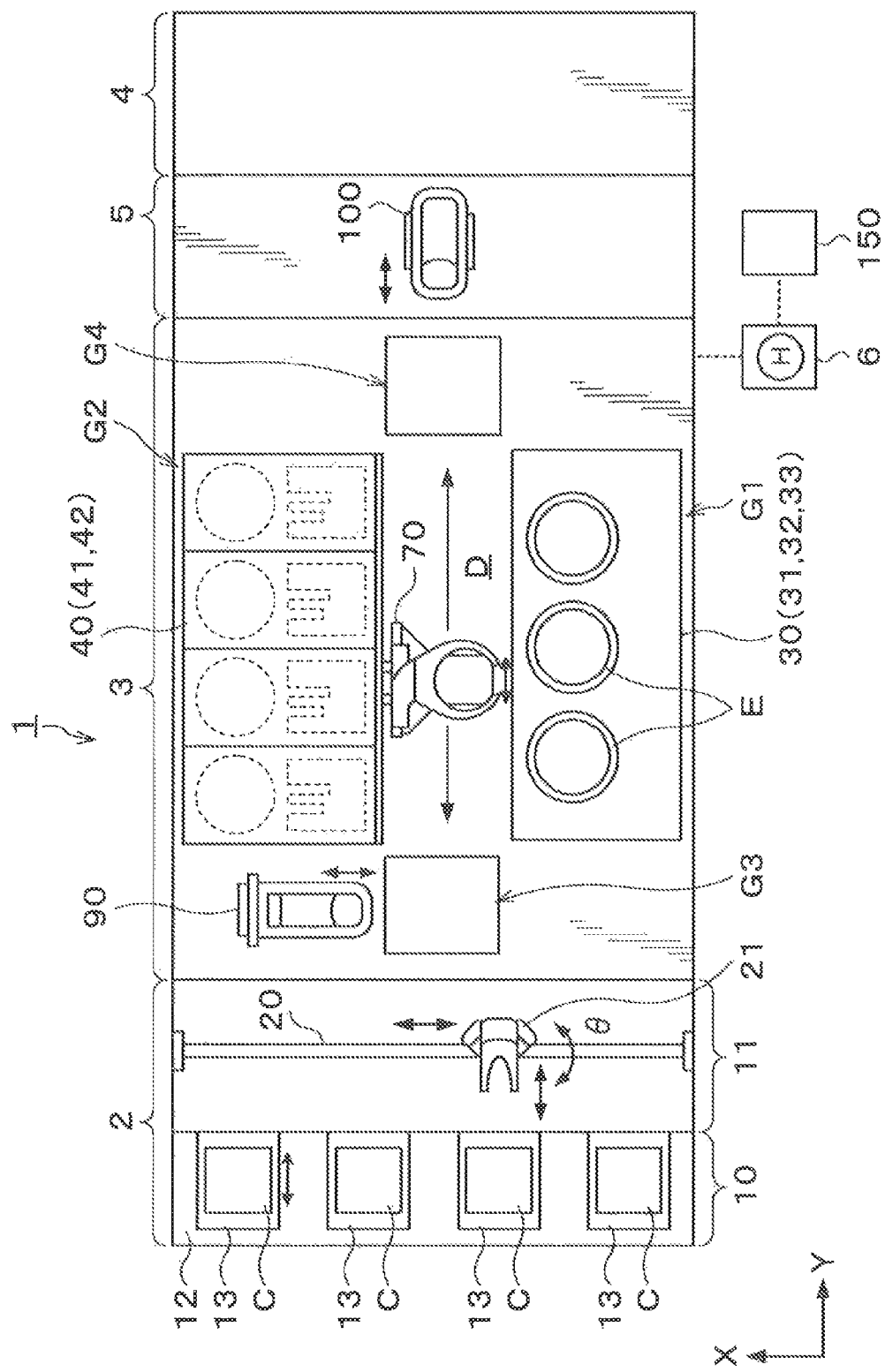
FIG. 1 is a plan view illustrating the outline of the internal configuration of a substrate treatment system according to this embodiment.
Figure 2:
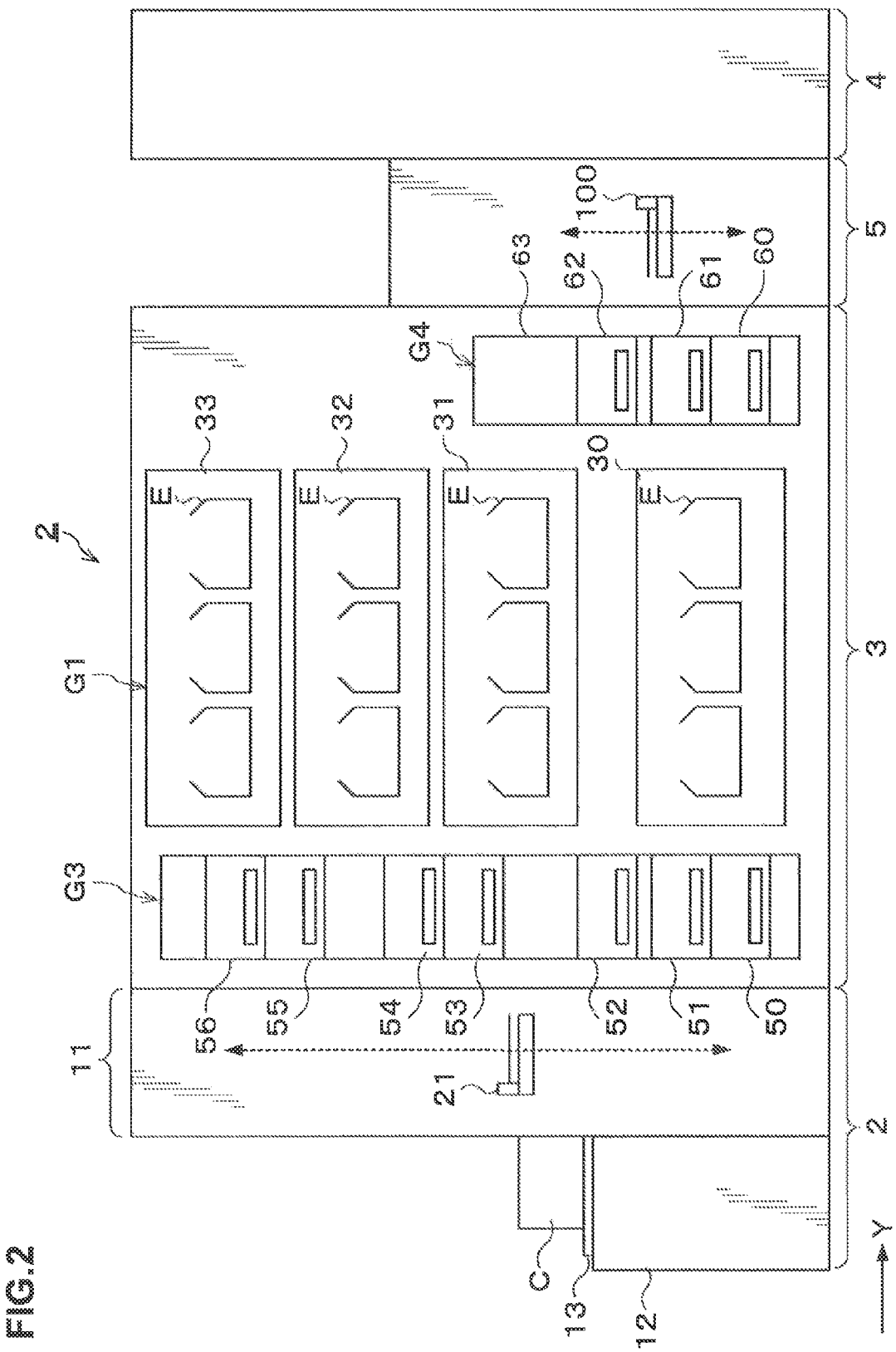
FIG. 2 is a side view illustrating the outline of the internal configuration of the substrate treatment system according to this embodiment.
Figure 3:
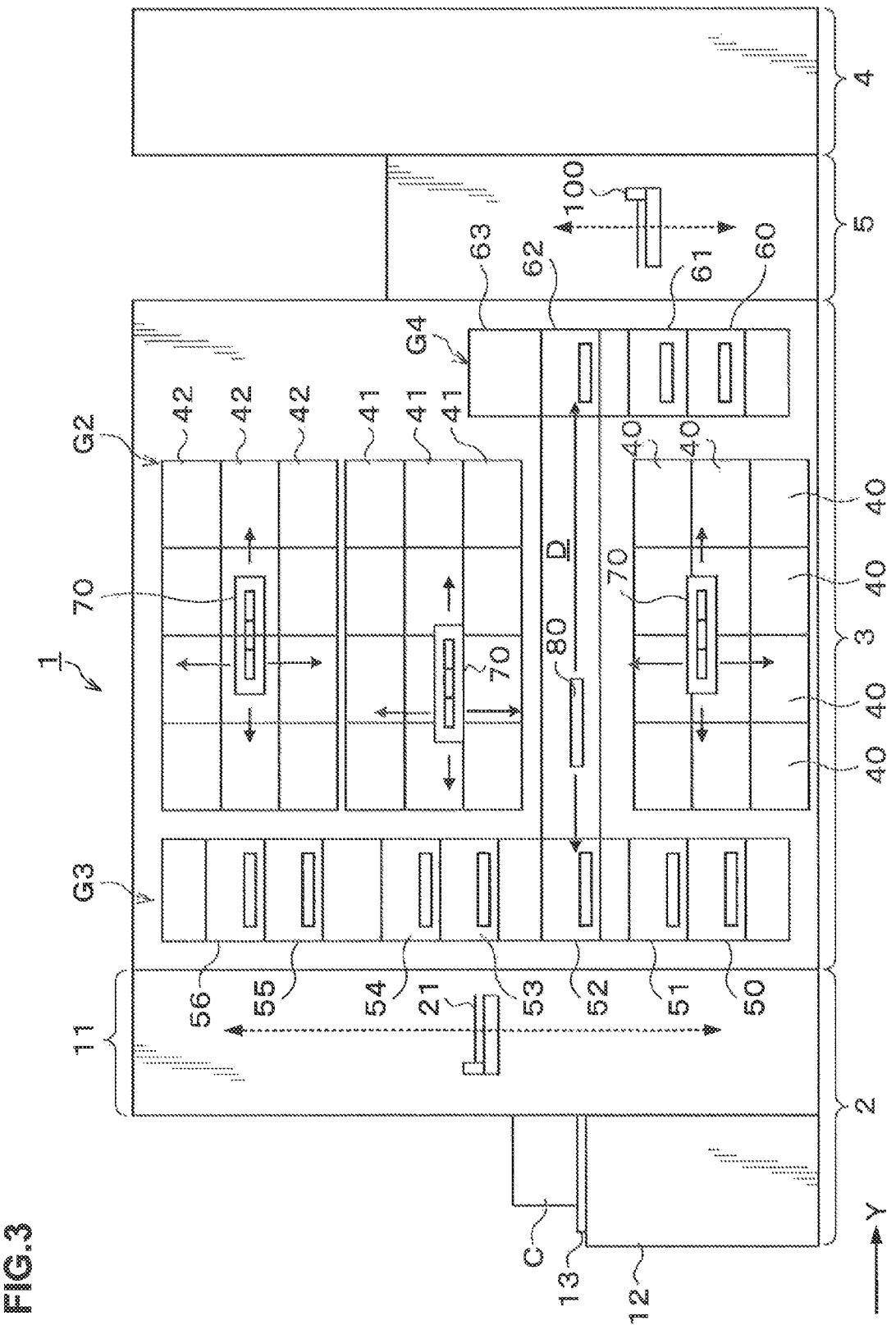
FIG. 3 is a side view illustrating the outline of the internal configuration of the substrate treatment system according to this embodiment.

Hereinafter, an embodiment of the present invention will be described. FIG. 1 is an explanatory view illustrating the outline of the internal configuration of a substrate treatment system 1 including an image processing apparatus according to this embodiment. FIG. 2 and FIG. 3 are side views illustrating the outline of the internal configuration of the substrate treatment system 1. Note that this embodiment will be described taking, as an example, the case where the substrate treatment system 1 is, for example, a coating and developing treatment system performing the photolithography treatment on a substrate.

The substrate treatment system 1 has, as illustrated in FIG. 1, a configuration in which, for example, a cassette station 2 as a transfer-in/out section into/from which a cassette C is transferred from/to, for example, the outside; a treatment station 3 as a treatment section including a plurality of various kinds of treatment units for performing predetermined treatments in a manner of single wafer treatment in a photolithography treatment; and an interface station 5 for delivering the wafer W to/from an exposure apparatus 4 adjacent to the treatment station 3, are integrally connected. The substrate treatment system 1 further has a control unit 6 controlling the substrate treatment system 1. To the control unit 6, a later-described image processing apparatus 150 is connected.

The cassette station 2 is divided into, for example, a cassette transfer-in/out section 10 and a wafer transfer section 11. For example, the cassette transfer-in/out section 10 is provided at the end portion on a Y-direction negative direction (the left direction in FIG. 1) side in the substrate treatment system 1. In the cassette transfer-in/out section 10, a cassette mounting table 12 is provided. On the cassette mounting table 12, a plurality of, for example, four mounting plates 13 are provided. The mounting plates 13 are provided side by side in a line in an X-direction (a top-down direction in FIG. 1) being the horizontal direction. On the mounting plates 13, cassettes C can be mounted when the cassettes C are transferred from/to the outside of the substrate treatment system 1.

In the wafer transfer section 11, a wafer transfer apparatus 21 is provided which is movable on a transfer path 20 extending in the X-direction as illustrated in FIG. 1. The wafer transfer apparatus 21 is also movable in the vertical direction and around the vertical axis (in a θ-direction), and thus can transfer the wafer W between the cassette C on each of the mounting plates 13 and a later-described delivery unit in a third block G3 in the treatment station 3.

In the treatment station 3, a plurality of for example, four blocks G1, G2, G3, G4 are provided each including various kinds of units. The first block G1 is provided on the front side (an X-direction negative direction side in FIG. 1) in the treatment station 3, and the second block G2 is provided on the rear side (an X-direction positive direction side in FIG. 1) in the treatment station 3. Further, the third block G3 is provided on the cassette station 2 side (a Y-direction negative direction side in FIG. 1) in the treatment station 3, and the fourth block G4 is provided on the interface station 5 side (a Y-direction positive direction side in FIG. 1) in the treatment station 3.

For example, in the first block G1, as illustrated in FIG. 2, a plurality of solution treatment units, for example, a developing treatment unit 30 performing developing treatment on the wafer W, a lower anti-reflection film forming unit 31 forming an anti-reflection film (hereinafter, referred to as a "lower anti-reflection film") under a resist film on the wafer W, a resist coating unit 32 applying a resist solution to the wafer W to form a resist film, and an upper anti-reflection film forming unit 33 forming an anti-reflection film (hereinafter, referred to as an "upper anti-reflection film") over the resist film on the wafer \V are four-tiered in order from the bottom.

For example, each of the units 30 to 33 in the first block G1 has a plurality of cups F in the horizontal direction each housing the wafer W therein at the time of treatment, and can treat the plurality of wafers W in parallel.

For example, in the second block G2, as illustrated in FIG. 3, thermal treatment units 40 each performing thermal treatment on the wafer W, adhesion units 41 as hydrophobic treatment apparatuses each performing a hydrophobic treatment on the wafer W, and edge exposure units 42 each exposing the outer peripheral portion of the wafer W are arranged one on top of the other in the vertical direction and side by side in the horizontal direction. The thermal treatment unit 40 has a thermal plate for mounting and heating the wafer W thereon and a cooling plate for mounting and cooling the wafer W thereon and therefore can perform both heat treatment and cooling treatment. Note that the numbers and the arrangement of the thermal treatment units 40, adhesion units 41, and edge exposure units 42 can be arbitrarily selected.

For example, in the third block G3, a plurality of delivery units 50, 51, 52, 53, 54, 55, 56 are provided in order from the bottom. Further, in the fourth block G4, a plurality of delivery units 60, 61, 62 and a defect inspection unit 63 are provided in order from the bottom.

As illustrated in FIG. 1, a wafer transfer region D is formed in a region surrounded by the first block G1 to the fourth block G4. In the wafer transfer region D, for example, a wafer transfer apparatus 70 is disposed.

The wafer transfer apparatus 70 has a transfer arm that is movable, for example, in the Y-direction, in the forward and backward direction, in the θ-direction, and in the vertical direction. The wafer transfer apparatus 70 can move in the wafer transfer region D and transfer the wafer W to a predetermined unit in the first block G1, the second block G2, the third block G3, and the fourth block G4 therearound. A plurality of, for example, four wafer transfer apparatuses 70 are arranged in the vertical direction as illustrated, for example, in FIG. 3 and can transfer the wafers W to predetermined units, in the respective blocks G1 to G4, at the similar heights as those of the wafer transfer apparatuses 70.

Further, in the wafer transfer region D, a shuttle transfer apparatus 80 linearly transferring the wafer W between the third block G3 and the fourth block G4 is provided.

The shuttle transfer apparatus 80 is configured to be linearly movable, for example, in the Y-direction in FIG. 3. The shuttle transfer apparatus 80 can move in the Y-direction while supporting the wafer W and transfer the wafer W between the delivery units 52 in the third block G3 and the delivery unit 62 in the fourth block G4.

As illustrated in FIG. 1, a wafer transfer apparatus 90 is provided on the X-direction positive direction side in the third block G3. The wafer transfer apparatus 90 has a transfer arm that is movable, for example, in the forward and backward direction, in the θ-direction, and in the vertical direction. The wafer transfer apparatus 90 can move in the vertical direction while supporting the wafer W to transfer the wafer W to each delivery unit in the third block G3.

In the interface station 5, a wafer transfer apparatus 100 is provided. The wafer transfer apparatus 100 has a transfer arm that is movable, for example, in the forward and backward direction, in the θ-direction, and in the vertical direction. The wafer transfer apparatus 100 can transfer the wafer W while supporting the wafer W, for example, by the transfer arm, to each delivery unit in the fourth block G4 and the exposure apparatus 4.

Next, the configuration of the defect inspection unit 63 will be described.

Figure 4:
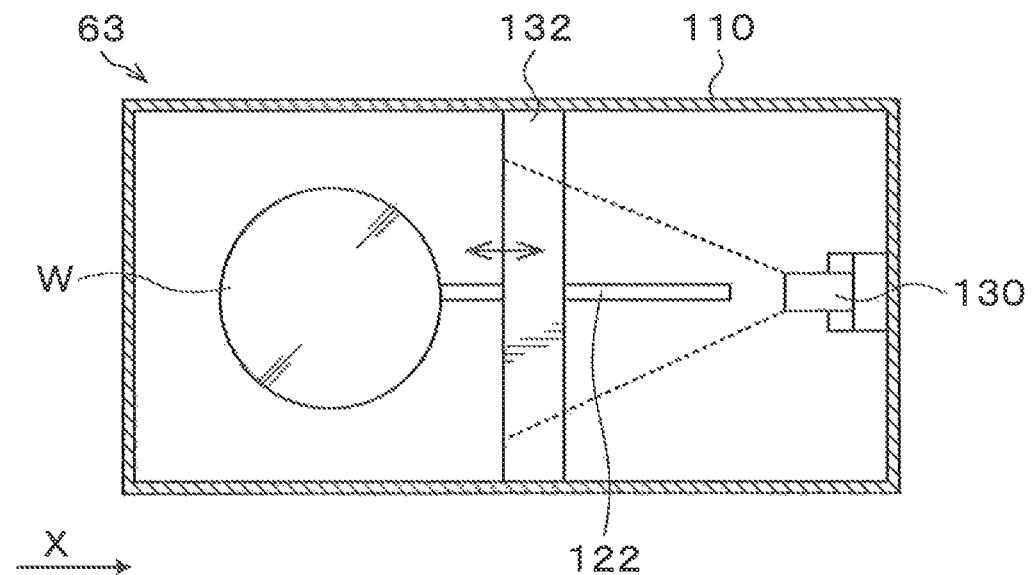
FIG. 4 is a transverse sectional view illustrating the outline of the configuration of a defect inspection apparatus.
Figure 5:
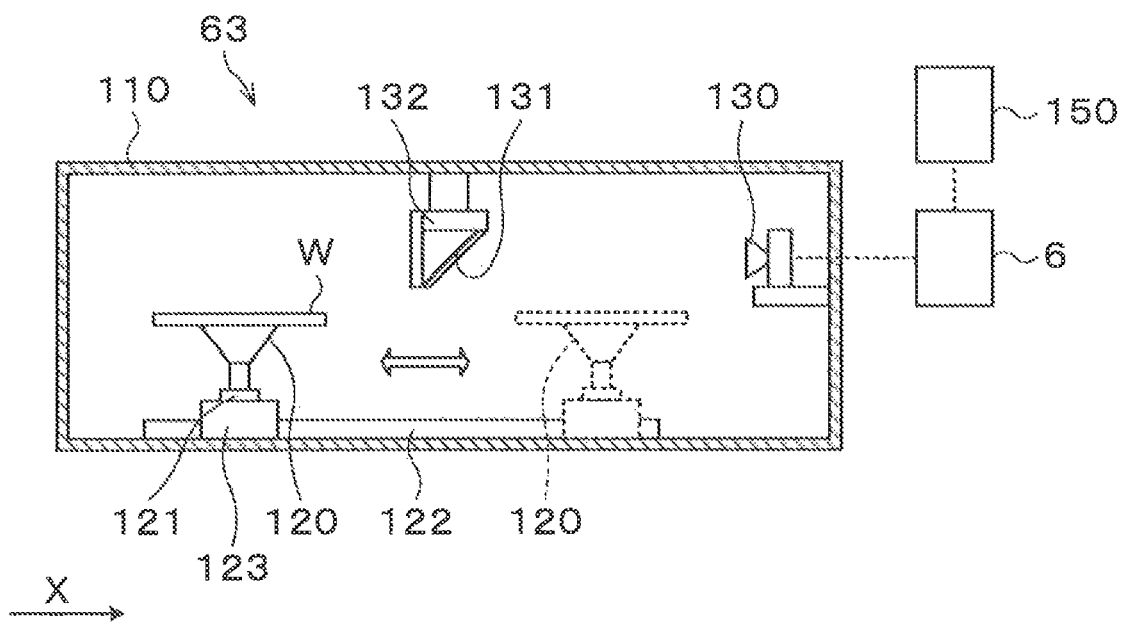
FIG. 5 is a longitudinal sectional view illustrating the outline of the configuration of the defect inspection apparatus.

The defect inspection unit 63 has a casing 110 as illustrated in FIG. 4. Inside the casing 110, a mounting table 120 is provided which mounts the wafer W thereon as illustrated in FIG. 5. This mounting table 120 freely rotates and stops by means of a rotary drive part 121 such as a motor. At the bottom surface of the casing 110, a guide rail 122 is provided which extends from one end side (an X-direction negative direction side in FIG. 5) to the other end side (an X-direction positive direction side in FIG. 5) in the casing 110. The mounting table 120 and the rotary drive part 121 are provided on the guide rail 122 and can move along the guide rail 122 by means of a drive apparatus 123.

An imaging device 130 is provided on the side surface on the other end side (the X-direction positive direction side in FIG. 5) in the casing 110. For the imaging device 130, for example, a wide-angle CCD camera is used, and the number of bits of the image is, for example, 8 bits. A half mirror 131 is provided near the upper middle portion of the casing 110. The half mirror 131 is provided at a position opposite to the imaging device 130 and inclined at 45 degrees from the vertical direction. An illumination device 132 is provided above the half mirror 131, and the half minor 131 and the illumination device 132 are fixed to the upper surface of the casing 110. The illumination from the illumination device 132 passes through the half mirror 131 and is applied downward. Accordingly, light reflected off an object lying below the illumination device 132 is further reflected by the half mirror 131 and captured into the imaging device 130. In other words, the imaging device 130 can pick up the image of the object lying within an irradiation region by the illumination device 132. Then, the picked up image of the wafer W to be inspected (substrate image) is inputted via the control unit 6 into the image processing apparatus 150.

The control unit 6 is composed of for example, a computer including, for example, a CPU and a memory, and has a program storage part (not illustrated). In the program storage part, a program is stored which controls defect inspection of the wafer W performed based on the substrate image picked up in the defect inspection unit 63. In addition, in the program storage part, programs are also stored for controlling the operations of the above-described various treatment units and the drive system such as the transfer apparatuses to realize predetermined operations in the substrate treatment system 1, such as the application of the resist solution to the wafer W, development, heat-treatment, delivery of the wafer W, control of each unit and so on. Note that the above-described programs may be ones which are recorded, for example, on a computer-readable storage medium H such as a hard disk (HD), compact disk (CD), magneto-optical disk (MO), or a memory card, and installed from the storage medium H into the control unit 6.

The program for controlling the defect inspection stored in the program storage part of the control unit 6 is for determining, for example, the presence or absence of defects possibly occurring on the wafer W, such as wind ripple, comet, striation, center mode, hot spot. Concretely, defect models created by combining images of templates simulating the defects of the wafer W and an image of a wafer W without defect are stored, and the substrate image picked up in the defect inspection unit 63 is compared with the defect models. Then, when the substrate image resembles any one of the defect models, it is determined that there is a defect, whereas when the substrate image does not resemble any one of the defect models, it is determined that there is no defect.

Figure 6:
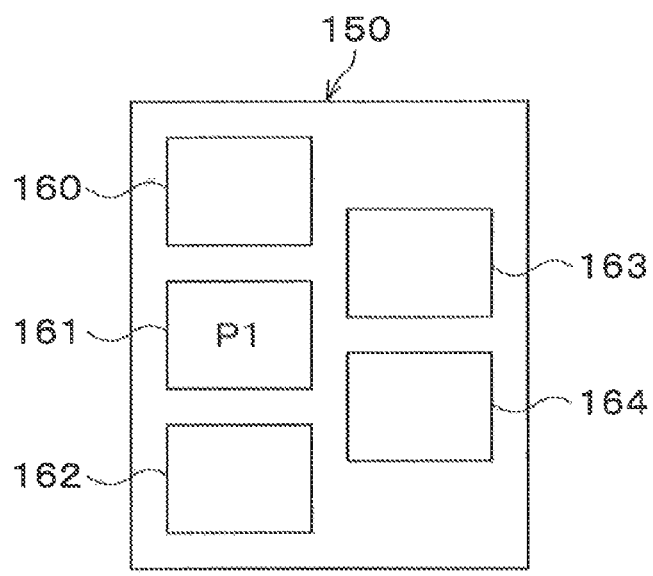
FIG. 6 is an explanatory view illustrating the outline of the configuration of an image processing apparatus.

Next, the configuration of the image processing apparatus 150 performing processing on the substrate image picked up in the defect inspection unit 63 will be described. The image processing apparatus 150 is composed of a general-purpose computer including, for example, a CPU, a memory and so on. The image processing apparatus 150 has, for example, a calculation part 160 making pixel values of the picked-up substrate image into a histogram, an arithmetic part 161 creating a tone curve based on the distribution of the pixel values in the histogram created by the calculation part, and a conversion part 162 converting the pixel values of the substrate image using the tone curve as illustrated in FIG. 6. Further, an input part 163 for inputting various kinds of information for creating the tone curve into the arithmetic part 161 and an output and display part 164 for outputting and displaying the substrate image are also provided in the image processing apparatus 150.

Figure 7:
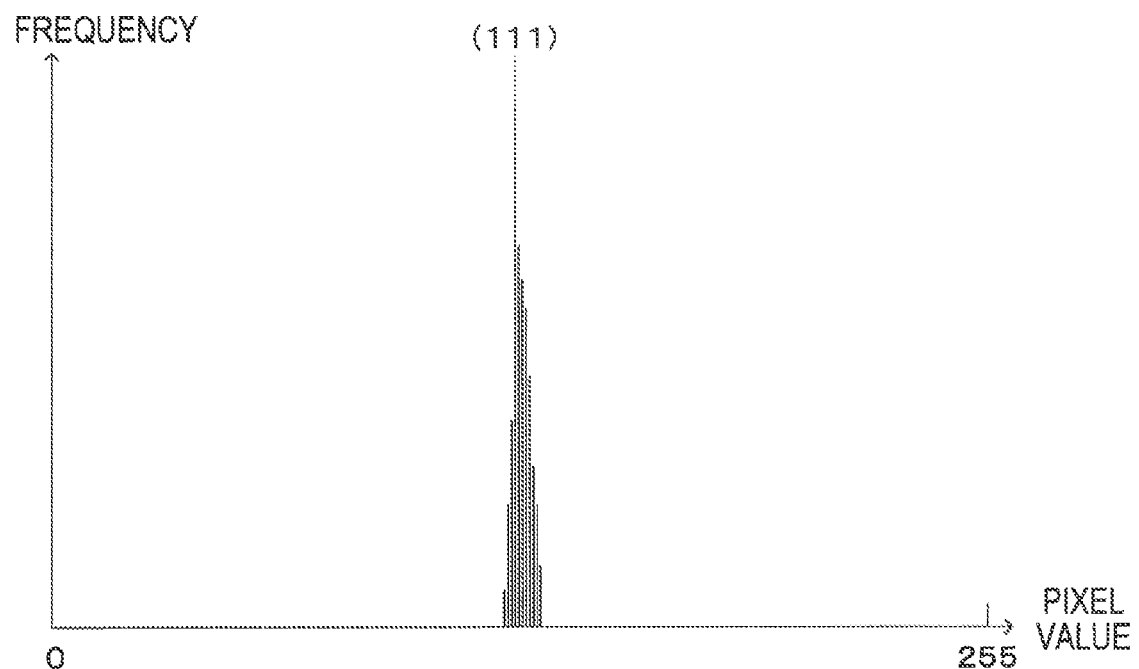
FIG. 7 is a histogram of a substrate image.

The calculation part 160 digitizes the substrate image inputted from the control unit 6 into the image processing apparatus 150 as pixel values for the entire substrate, and obtains the histogram of the substrate image as illustrated in FIG. 7. In the histogram in FIG. 7, the pixel value is presented on the horizontal axis, and the frequency is presented on the vertical axis. Note that the substrate image is generally composed of three colors of RGB (Red, Green, Blue). Therefore, the substrate image can be made into a histogram for each of R, G, B, and there is no difference in the method of image processing among R, G, B. Accordingly, this embodiment will be described without particularly specifying R, G, B.

The arithmetic part 161 analyzes the distribution of the pixel values in the histogram calculated in the calculation part 160 and creates the tone curve used for the processing of the substrate image. The tone curve created in the arithmetic part 161 is a periodic function of a predetermined amplitude and a predetermined period. Hereinafter, a method of creating the tone curve will be described.

In the arithmetic part 161, a program P1 is stored which creates the tone curve for obtaining an output pixel value Y after conversion based on the following Expression (1)

$$Y = \{(2^C/2) - N\} \times [\sin\{(X-A)/B\} + 1] \quad (1)$$

As is clear from Expression (1), the tone curve created in the arithmetic part 161 is a trigonometric function. C in Expression (1) is the number of bits of the substrate image, and N is the constant determining the amplitude of the tone curve obtained by Expression (1). X is the pixel value in the substrate image picked up in the defect inspection unit 63, A is the phase of the trigonometric function, and B is the period of the trigonometric function. Here, the principle of the image processing in the present invention using the tone curve in Expression (1) will be briefly described.

In order to emphasize the contrast of the image, the image is made into a histogram, and a tone curve having a steep slope in a region near the mode value in the histogram is used. However, in a tone curve T in the shape illustrated in FIG. 20, the contrast in a region other than a region U near the mode value remarkably decreases as has been described. The present inventors focused attention on that a tone curve having a steep slope over the entire region of the histogram can be obtained by creating the tone curve based on the function whose value periodically and repeatedly changes, that is, the periodic function.

Concretely, for example, when using a trigonometric function as the tone curve, the value of the tone curve varies from the minimum value to the maximum value in every half of the period of the trigonometric function. Accordingly, the phase of the trigonometric function is adjusted so that the value between the minimum value and the maximum value (namely, when the value of sin θ is 0) matches the mode value in the histogram, and the period is set so that the integral value of the right and left pixel value ranges about the mode value of the tone curve has a predetermined ratio to the integral value of the whole histogram, thereby making it possible to make the slope of the tone curve T steep in the right and left pixel value ranges R about the mode value in the histogram, for example, as illustrate in FIG. 8. The present invention is made based on such an idea, and a method of concretely obtaining the tone curve T in Expression (1) according to this embodiment will be described next.

First, since the imaging device 130 for the 8-bit image is used in the defect inspection unit 63, the value of C in Expression (1) is "8." In this case, the range of the pixel value X of the substrate image has 256 graduations, in other words, the possible value of the pixel value X of the substrate image inputted into Expression (1) is an integer of 0 to 255. Further, the constant N in Expression (1) can be arbitrarily set within a range where the value of the output pixel value Y to the pixel value X of the substrate image being the input pixel value is 0 to 255 due to the nature of the tone curve. Concretely when the value of C is "8," the constant N can be set within a range of ½ to 128. Note that an increase of the value of the constant N leads to a decrease of a range width of the value that the output pixel value Y can take, resulting in a loss of the benefit of the image conversion using the tone curve. Therefore, it is generally preferable to set the value of the constant N to "1". When the value of the output pixel value Y is set to a range of 0 to 255, the value of the constant N should be "½." However, that the value of the output pixel value Y is preferably an integer since each pixel value of R, G, B expresses the brightness of the color through use of an integer value, and that the image after processing when the maximum value of the output pixel value Y is "254" is not greatly different from the image when the maximum value is set to "255," are the reasons why the constant N is set to "1." Accordingly, the case where the value of N is set to "1" and the amplitude of Expression (1) is set to "127," that is, the value of the output pixel value Y is set to 0 to 254 will be described in this embodiment. Note that if the value of the output pixel value Y to the pixel value X of the substrate image is not an integer due to setting of the constant N, the conversion part 162 may perform processing to appropriately round the value of the output pixel value Y and output the value as an integer.

Next, the value of the pixel value being the mode value in the histogram illustrated in FIG. 7 is obtained as the value of the phase A. Assuming that the mode value, that is, the pixel value that is the most frequent pixel value is, for example, "111" in the histogram illustrated in FIG. 7, the value of the phase A in this case is "111." In this manner, the use of the mode value as the value of the phase A can match the center value of the amplitude of the tone curve, that is, the center of a region K illustrate in FIG. 8 with the mode value.

Figure 8:
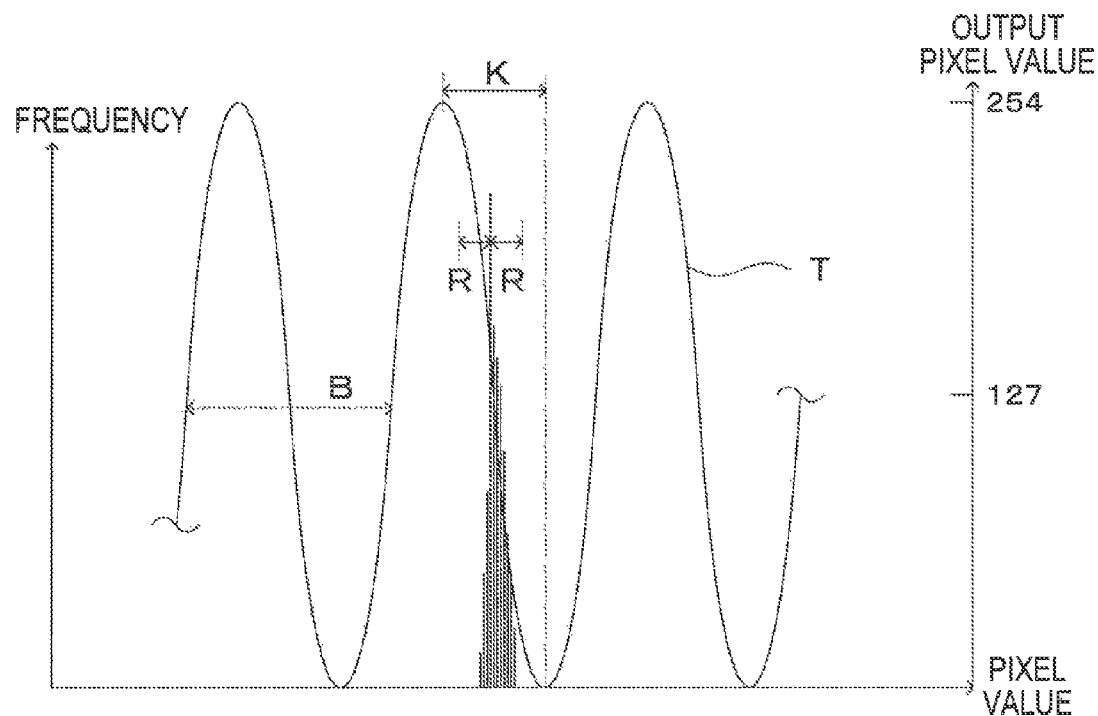
FIG. 8 is an explanatory view illustrating the relation between a tone curve according to image processing of this embodiment and the histogram of the substrate image.
Figure 9:
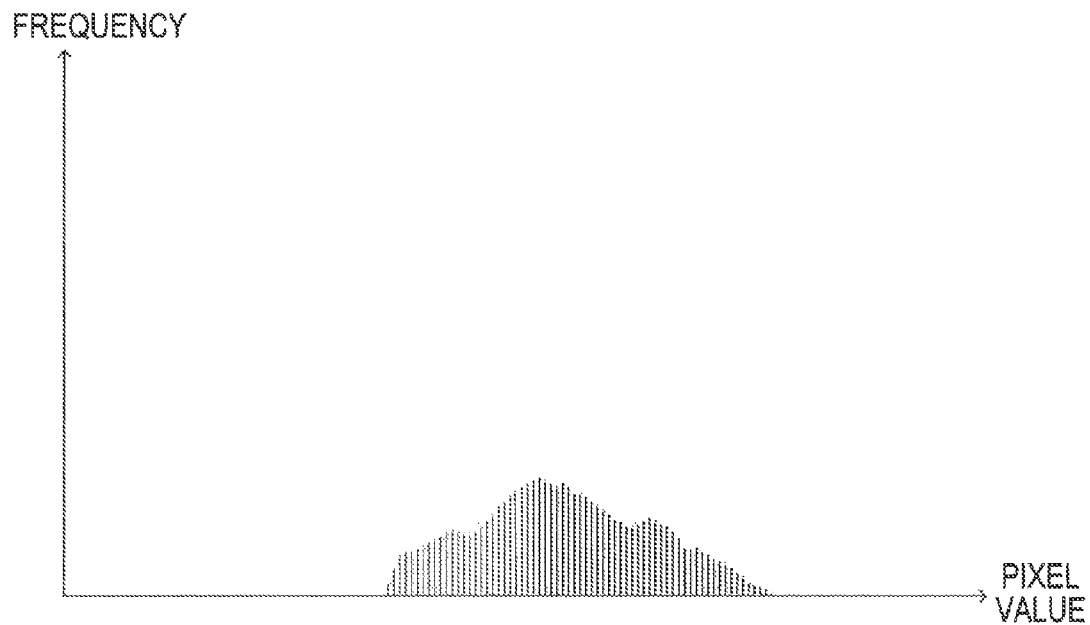
FIG. 9 is a histogram of the substrate image.

The value of the period represented by B is set by finding the pixel value range R so that the integral value of the right and left pixel value ranges R about the mode value in the histogram is at a predetermined ratio to the integral value of the whole histogram. The predetermined ratio is arbitrarily determined depending on the shape of the histogram of the substrate image. The period B represents the period of the function expressed by Expression (1) as illustrated in FIG. 8, in which the slope of the tone curve decreases as the value of the period B increases, and the slope of the tone curve increases as the value of the period B decreases. Therefore, in the case where the histogram takes a shape having a sharp peak as illustrated in FIG. 8, the predetermined ratio may be set to a high value that is 90% or more. This is because in the case where the histogram conversely has a smooth curve as illustrated in FIG. 9, the period increases when the value of the predetermined ratio increases, and the degree of emphasis of the contrast in the substrate image after conversion using the tone curve also decreases.

Since the pixel value in the histogram is a discrete value, an integral value F of the whole histogram is expressed by the following Expression (2) as a total sum of the frequency of all pixel values. Note that Expression (2) expresses the integral value in the 8-bit image, $$F = \sum_{i=0}^{255} H(i) \qquad (2)$$

H(i) in Expression (2) is the frequency of each pixel value (i=0 to 255).

Further, a sum of the frequencies in the right and left pixel value ranges R about the mode value is expressed by the following Expression (3).

$$J = \sum_{i=A-1}^{A-R} H(i) + \sum_{i=A+1}^{A+R} H(i) \qquad (3)$$

Accordingly a ratio L of the total sum J of the frequencies in the pixel value ranges R to the integral value F of the whole histogram is expressed as in the following Expression (4).

$$L = J/F \times 100 \qquad (4)$$

Figure 10:
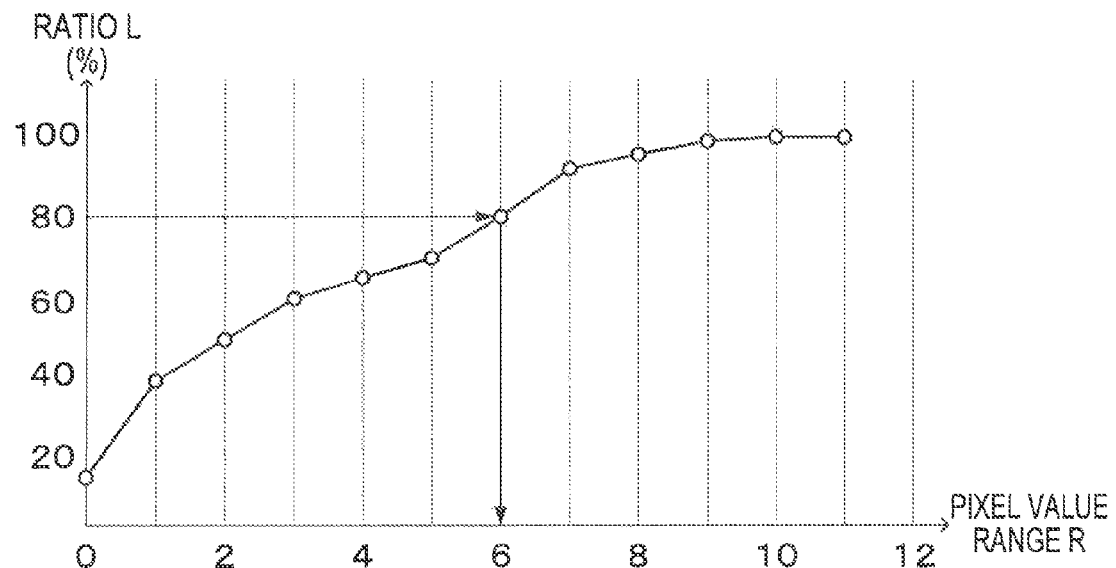
FIG. 10 is an explanatory view illustrating the relation between a pixel value range and a ratio of a total sum of frequencies within pixel value ranges R to an integral value of the whole histogram.

From Expression (4), for example, a graph representing the relation between the pixel value ranges R and the ratio L of the integral value as illustrated in FIG. 10 is obtained. Then, the ratio L is arbitrarily set according to the distribution of the pixel values in the histogram, and the pixel value ranges R are obtained from the graph in FIG. 10 and set as the value of the period B. Note that the ratio L is set, for example, 80% in this embodiment. Then, the ratio L becomes roughly 80% in the case where the pixel value ranges R are "6" and the value of the period B is thus set to "6."

Then, when the values of the above-described bit number C, constant N, phase A, and period B are substituted into Expression (1), Expression (1) is expressed as a trigonometric function of Y and X like the following Expression (5).

$$Y = (127) \times [\sin\{(X-111)/6\}+1] \qquad (5)$$

Figure 11:
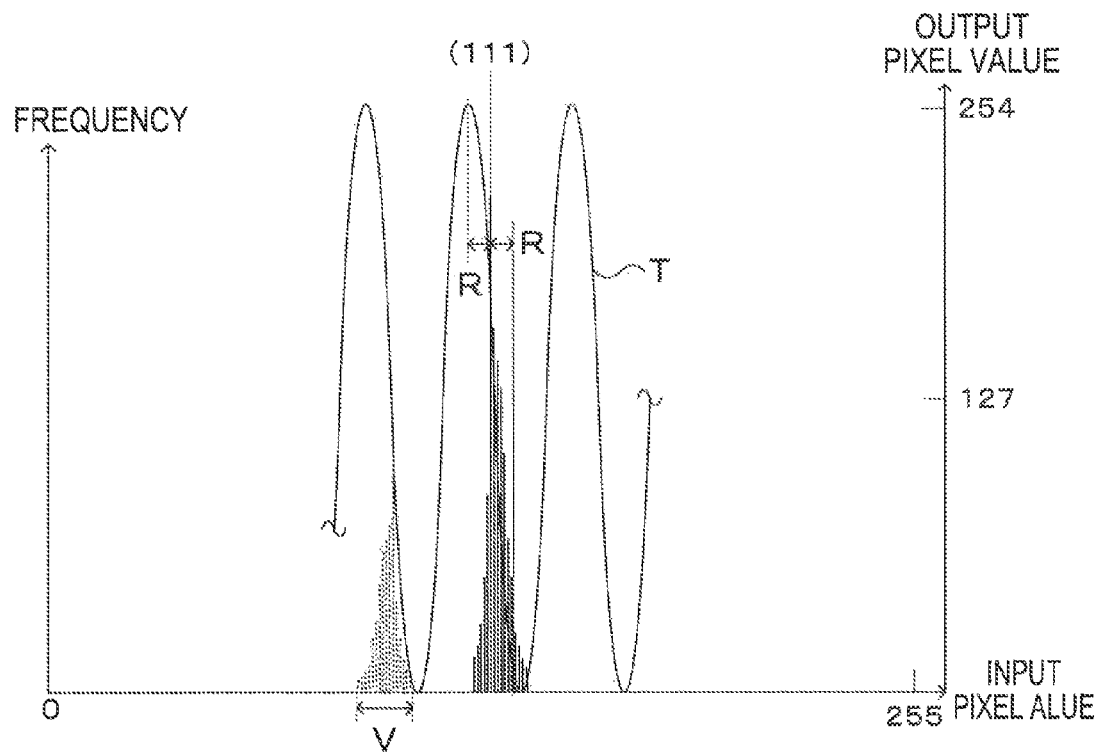
FIG. 11 is an explanatory view illustrating the relation between the tone curve according to the image processing of this embodiment and the histogram of the substrate image.

Then, when Expression (5) is drawn as a graph such that the horizontal axis represents the pixel value X of the input image and the vertical axis represents the pixel value Y after conversion, a tone curve T in the shape of a trigonometric function in which 80% of the total sum of the pixel values in the histogram are included in a half region of the period B is obtained as illustrated in FIG. 11.

Next, the conversion part 162 performs image processing on the substrate image by using the tone curve T illustrated in FIG. 11. In this case, the tone curve T is a trigonometric function with a phase of "111" and a period of "6" as illustrated in FIG. 11, so that when the pixel value in the histogram becomes "111" being the mode value, the value of the output pixel value Y becomes "127" being the intermediate value, and 80% of the integral value F of the whole histogram illustrated in FIG. 7 falls within a region where the value of the output pixel value Y expressed by the tone curve T increases from 0 to 255 (the region within the pixel value ranges R illustrated in FIG. 11). Accordingly, the tone curve T obtained from Expression (1) and the histogram in FIG. 7 has a slope steep in the pixel value ranges R near the mode value in the histogram, and the image in the pixel value ranges R can be converted into an image with a high contrast. Further, since the tone curve T is the trigonometric function in which the maximum value and the minimum value are periodically repeated, the image with a high contrast can be obtained also from the pixel values existing in a region. V outside the pixel value ranges R as illustrated in FIG. 11.

The substrate image converted and processed in the conversion part 162 is outputted to the output and display part 164 in which the processed image is displayed.

It is also possible to obtain an optimum tone curve T by arbitrarily inputting in this event the values of the phase A and the period B from the input part 163 based on the shape of the histogram. Note that the input part 163 may be an operation terminal such as a keyboard, and may be various operation buttons displayed on the output and display part 164 when the output and display part 164 is a touch panel.

The substrate treatment system 1 according to this embodiment is configured as described above, and the treatment on the wafer W performed in the substrate treatment system 1 configured as described above will be described next.

In the treatment on the wafer W, the cassette C housing a plurality of wafers W therein is mounted on a predetermined mounting plate 13 in the cassette transfer-in/out section 10. Then, the wafers W in the cassette C are sequentially taken out by the wafer transfer apparatus 21 and transferred, for example, to the delivery unit 53 in the third block G3 in the treatment station 3.

Then, the wafer W is transferred by the wafer transfer apparatus 70 to the thermal treatment unit 40 in the second block G2 and temperature-regulated. Thereafter, the wafer W is transferred by the wafer transfer apparatus 70, for example, to the lower anti-reflection film forming unit 31 in the first block: G1, where a lower anti-reaction film is formed on the wafer W. The wafer W is then transferred to the thermal treatment unit 40 in the second block G2 and subjected to heat treatment. The wafer W is then returned to the delivery unit 53 in the third block G3.

Then, the wafer W is transferred by the wafer transfer apparatus 90 to the delivery unit 54 in the same third block G3. Thereafter, the wafer W is transferred by the wafer transfer apparatus 70 to the adhesion unit 41 in the second block G2 and subjected to a hydrophobic treatment. The wafer W is then transferred by the wafer transfer apparatus 70 to the resist coating unit 32, where a resist film is formed on the wafer W. The wafer W is then transferred by the wafer transfer apparatus 70 to thermal treatment unit 40 and subjected to pre-baking. The wafer W is then returned by the wafer transfer apparatus 70 to the delivery unit 55 in the third block G3.

Then, the wafer is transferred by the wafer transfer apparatus 70 to the upper anti-reflection film forming unit 33, where an upper anti-reflection film is formed on the wafer W. The wafer W is then transferred by the wafer transfer apparatus 70 to the thermal treatment unit 40, and heated and temperature-regulated. The wafer W is then transferred to the edge exposure unit 42 and subjected to edge exposure processing.

The wafer W is then returned by the wafer transfer apparatus 70 to the delivery unit 56 in the third block G3.

The wafer W is then transferred by the wafer transfer apparatus 90 to the delivery unit 52 and transferred by the shuttle transfer apparatus 80 to the delivery unit 62 in the fourth block G4. The wafer W is then transferred by the wafer transfer apparatus 100 in the interface station 7 to the exposure apparatus 4 and subjected to exposure processing. The wafer W is then transferred by the wafer transfer apparatus 100 to the delivery unit 60 in the fourth block: G4. The wafer W is then transferred by the wafer transfer apparatus 70 to the thermal treatment unit 40 and subjected to post-exposure baking. The wafer W is then transferred by the wafer transfer apparatus 70 to the developing treatment unit 30 and developed. After the development, the wafer W is transferred by the wafer transfer apparatus 70 to the thermal treatment unit 40 and subjected to post-baking.

The wafer W is then transferred by the wafer transfer apparatus 70 to the delivery unit 50 in the third block G3, and then transferred by the wafer transfer apparatus 21 in the cassette station 2 to the cassette C on the predetermined mounting plate 13. Thus, a series of photolithography processes end.

Thereafter, the wafer W is transferred by the wafer transfer apparatus 70 to the delivery unit 62 in the fourth block G4. Then, the wafer W is transferred by the wafer transfer apparatus 100 to the defect inspection unit 63 and subjected to inspection of the wafer W. Data on the substrate image picked up by the imaging device 130 in the defect inspection unit 63 is inputted via the control unit 6 into the image processing apparatus 150.

In the image processing apparatus 150, the tone curve T is created based on the histogram of the substrate image and Expression (1), and the pixel values of the picked-up substrate image are converted using the tone curve T. Then, the control unit 6 compares the converted substrate image with the defect models. When the converted substrate image does not resemble any one of the defects, it is determined that there is no defect occurring in the wafer W. Contrarily, when a defect model, resembling the image of the wafer W to be inspected, it is determined that there is a defect corresponding to the defect model occurring in the wafer W. Note that the determination of the presence or absence of the defect may be performed by an operator visually checking the image on the output and display part 164.

The wafer W through the defect inspection is transferred by the wafer transfer apparatus 100 to the delivery unit 62. Thereafter, the wafer W is transferred via the wafer transfer apparatus 70 and the wafer transfer apparatus 21 to the cassette C on the predetermined mounting plate 13, and the series of photolithography processes and the inspection on the wafer W by the defect inspection unit 63 are repeatedly performed.

According to the above embodiment, the tone curve T composed of the trigonometric function is used for converting the pixel values of the substrate image, thus making it possible to the slope of the tone curve T steep in the whole region of the histogram. Accordingly, performing the image processing using the tone curve makes it possible to create a substrate image with a high contrast even from the image picked up using the imaging device 130 with a smaller number of bits, and to provide an image with a high contrast also on the pixel values existing in the region V outside the image value ranges R. This enables improvement in visibility of the substrate image picked up by the defect inspection unit 63 and resultantly performance of a defect inspection with a high accuracy. Further, because of use of the trigonometric function, the contrast of the image can be easily adjusted by changing the phase and the period.

In particular, an optimal tone curve T can be automatically created by using Expressions (1) to (4), so that an image with a high contrast can be easily obtained without depending on the level of skill of the operator.

Further, since the image processing apparatus 150 has the input part 163, a tone curve for obtaining an image with a higher contrast can be created corresponding to the distribution of the pixel values in the histogram. Concretely, taking, as an example, the case of an image having, for example, a histogram which is not in a symmetrical shape about the mode value but has a distribution of the pixel values deviated to one of the right side and the left side of the mode value in the histogram as illustrated, for example, in FIG. 12, the mode value is not set as the value of the phase A, but the pixel value being the intermediate value in a region W where the pixel values are deviated (A1 in FIG. 12) is set as the phase A, and the period B is set taking the intermediate value A1 as a center. This makes it possible to precisely match the width of the tone curve T with the histogram, resulting in a substrate image with a higher contrast and better visibility. Further, also when the pixel values in the region V and the phase of the tone curve T do not satisfactorily match with each other in FIG. 11 and therefore the image in the region V is not appropriately displayed, the phase A and the period B can be adjusted so that the images in both of the pixel value ranges R and the region V are appropriately displayed.

Note that though the values of the phase A and the period B of the periodic function are adjusted for matching the tone curve T with the mode value and the peak value in the histogram of the pixel values in the above embodiment, the matching may be made, for example, by combining two or more periodic, functions to create the tone curve T. Hereinafter, the case where two or more periodic functions are combined to match the tone curve will be described.

Figure 13:
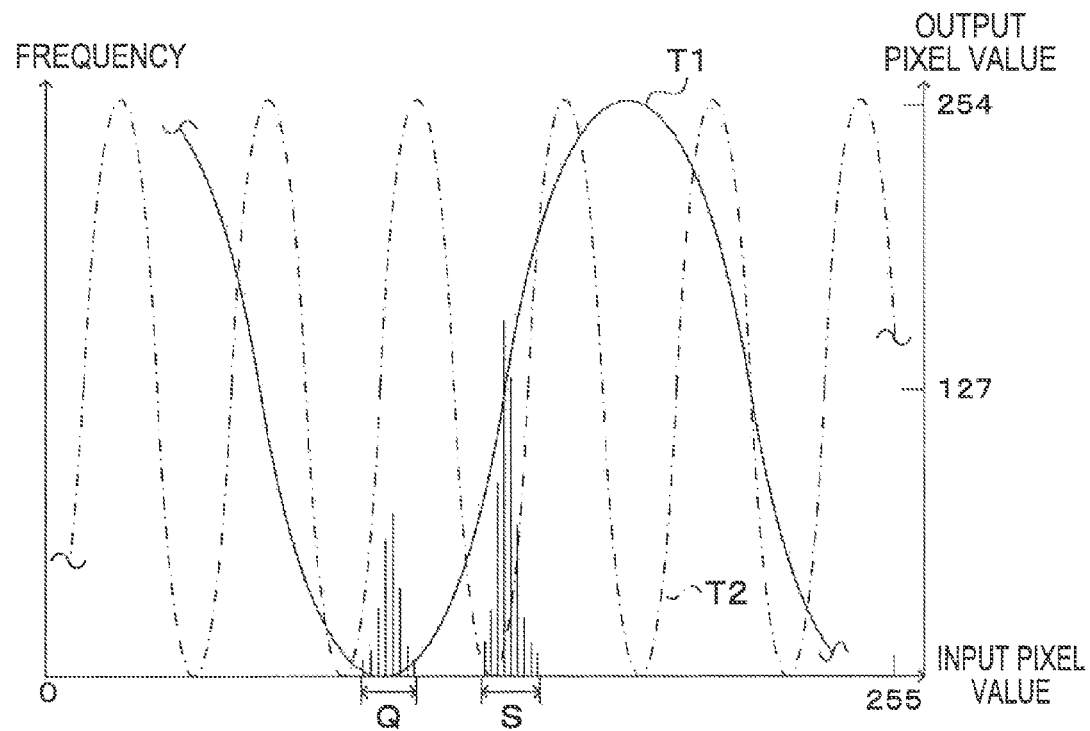
FIG. 13 is an explanatory view illustrating the relation between the histograms of the substrate image existing in a plurality of regions and a plurality of tone curves obtained correspondingly to the histograms.

When there are peaks of the input pixel values respectively in a region S and in another region Q different from the region S in the histogram of the substrate image as illustrated, for example, in FIG. 13 and a tone curve T1 is obtained for the region 5, the vicinity of the peak of the amplitude of the tone curve T1 sometimes overlaps with the other region Q. In this case, use of the tone curve T1 as it is conversely decreases the contrast in the region Q. Accordingly, it is conceivable to adjust the values of the phase A and the period B of the tone curve T1 in order to also ensure the contrast in the region Q.

However, if the values of the phase A and the period B of the tone curve T1 are adjusted in consideration of the contrast in the region Q, the contrast in the region S is not always optimum in some cases. Hence, in addition to the tone curve T1 corresponding to the region 5, a tone curve T2 corresponding to the peak of the input pixel values existing in the region Q is separately and independently obtained based on Expression (1). In short, the tone curve T2 having a slope that is steep in the region Q is obtained as illustrated by a chain line in FIG. 13. In this case, the tone curve 12 is different from the tone curve T1 either in the period B or the phase A.

Next, the tone curve T1 corresponding to the region S and the tone curve T2 corresponding to the region Q are combined to obtain a tone curve T3. In this case, assuming that the output pixel value converted using the tone curve T1 corresponding to the region S is Y1 and the output pixel value converted using the tone curve T2 corresponding to the region Q is Y2, the expression to obtain an output pixel value Y3 converted using the tone curve T3 made by combining the tone curve T1 and the tone curve T2 is expressed like the following Expression (6).

$$Y3 = (a \times Y1) + \{(1-a) \times Y2\} \quad (6)$$

Here, "a" in Expression (6) is a weighting coefficient when combining the tone curve T1 for obtaining the output pixel value Y1 and the tone curve T2 for obtaining the output pixel value Y2, and can take an arbitrary value between 0 and 1. Note that when "a" is set to 1, the tone curve 13 becomes the same as the tone curve T1, and when "a" is set to 0 (zero), the tone curve T3 become the same as the tone curve T2.

Figure 14:
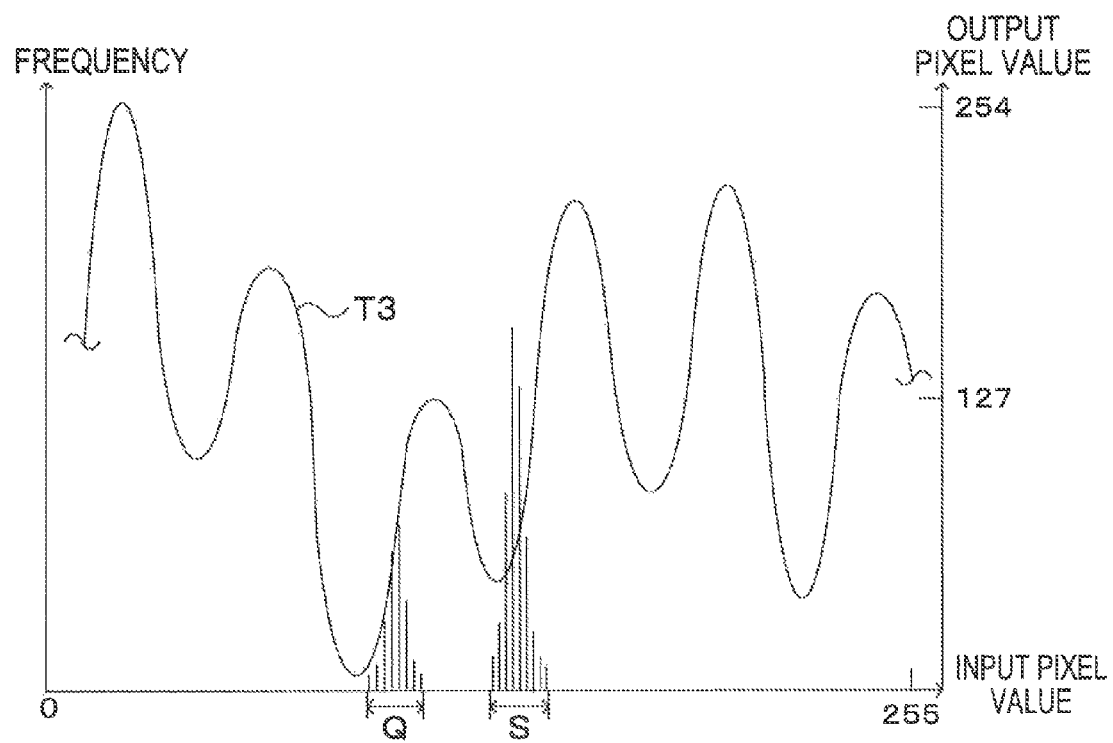
FIG. 14 is an explanatory view illustrating the relation between a tone curve obtained by combining the plurality of tone curves and the histogram of the substrate image.

For example, when "a" is set to 0.5, the tone curve T1 and the tone curve T2 are combined at the same weight. In this case, the tone curve T3 obtained by combination is a tone curve made by simply combining the tone curve T1 and the tone curve T2 at a ratio of 1 to 1 that is the half of the output pixel values after combination as illustrated in FIG. 14.

Figure 15:
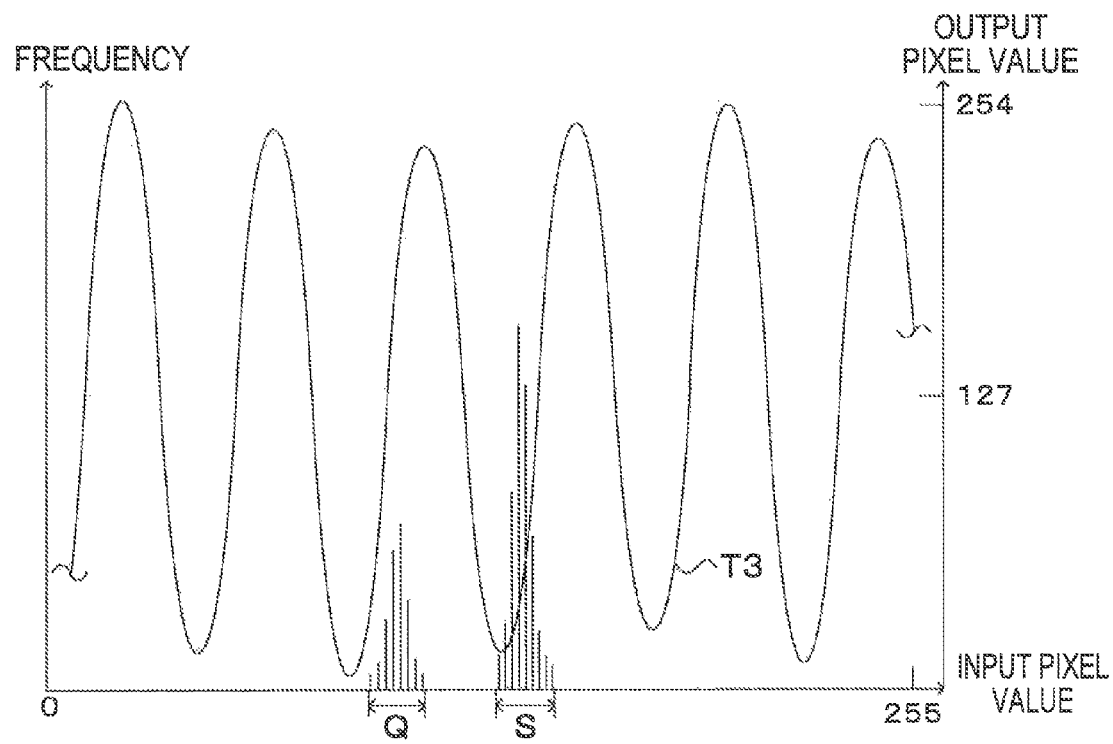
FIG. 15 is an explanatory view illustrating the relation between a tone curve obtained by combining the plurality of tone curves and the histogram of the substrate image.
Figure 16:
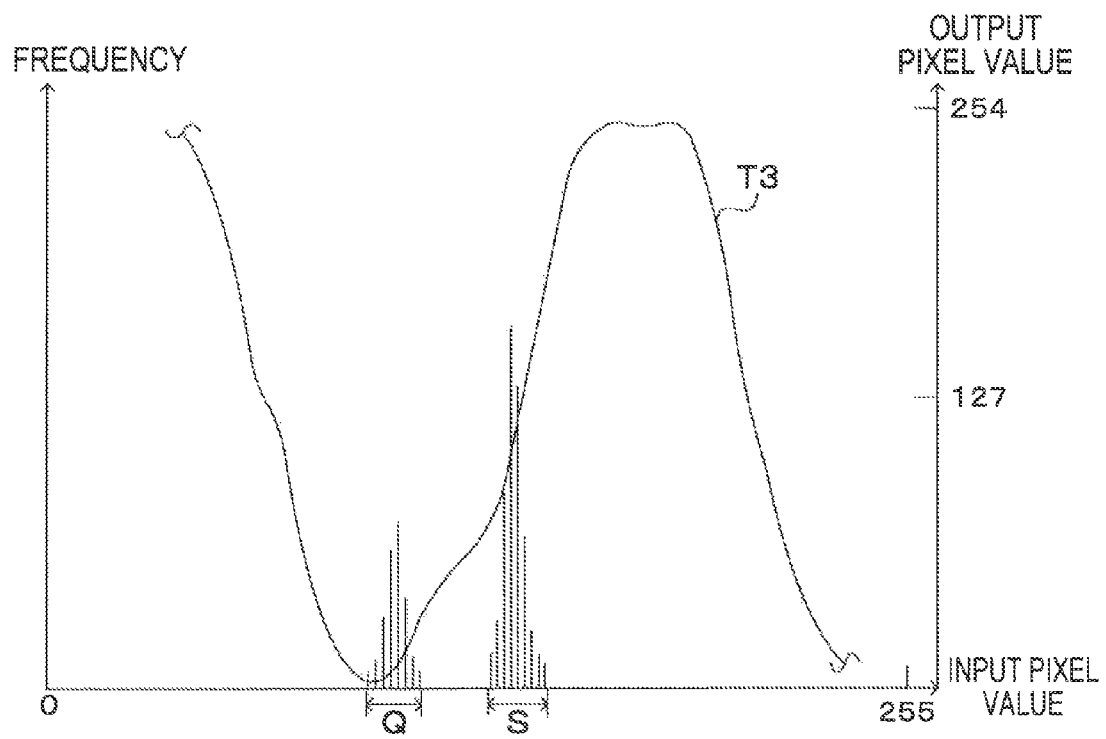
FIG. 16 is an explanatory view illustrating the relation between a tone curve obtained by combining the plurality of tone curves and the histogram of the substrate image.

For example, when "a" is set to 0.1, the shape of the tone curve T3 after combination is the one in which the shape of the tone curve T1 is dominant as illustrated in FIG. 15. Conversely, when "a" is set to 0.9, the shape of the tone curve T3 is the one in which the shape of the tone curve T2 is dominant as illustrated in FIG. 16. Note that by setting "a" to 0.1 or 0.5 as illustrated in FIG. 14 or FIG. 15, the tone curve T3 whose slope is steep both in the region S and the region Q can be obtained in this embodiment. Therefore, according to the above embodiment, it is possible to convert the input pixel values existing in a plurality of regions to obtain an image with a high contrast in any of the regions by combining a plurality of tone curves to obtain the tone curve T3.

Figure 17:
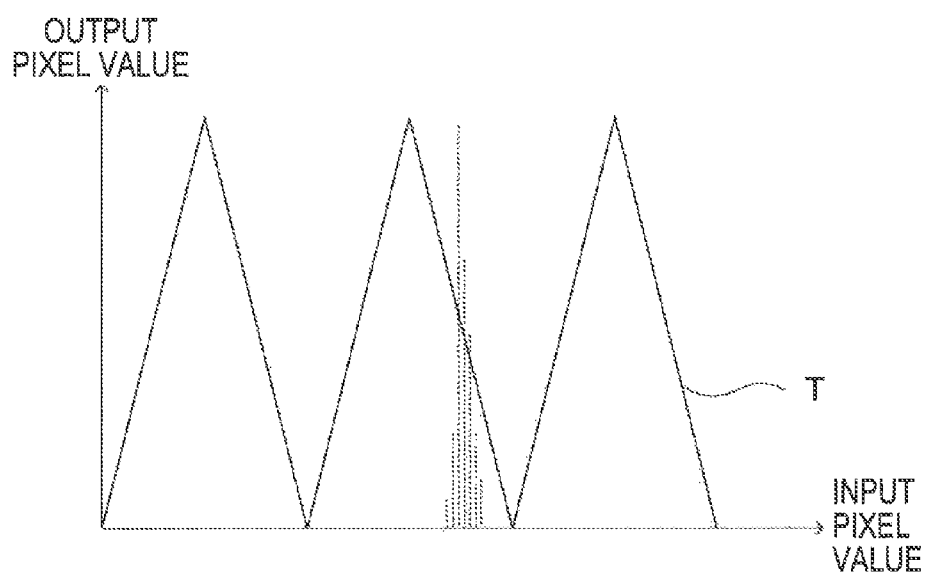
FIG. 17 is an explanatory view illustrating the relation between a tone curve according to the image processing of this embodiment and the histogram of the substrate image.
Figure 24:
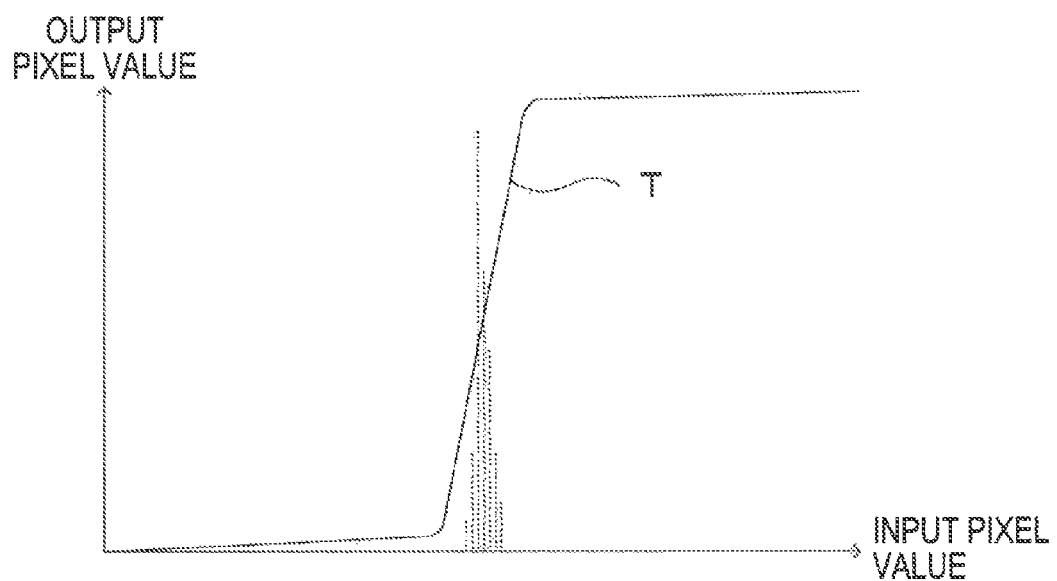
FIG. 24 is a tone curve deformed by a conventional method.
Figure 25:
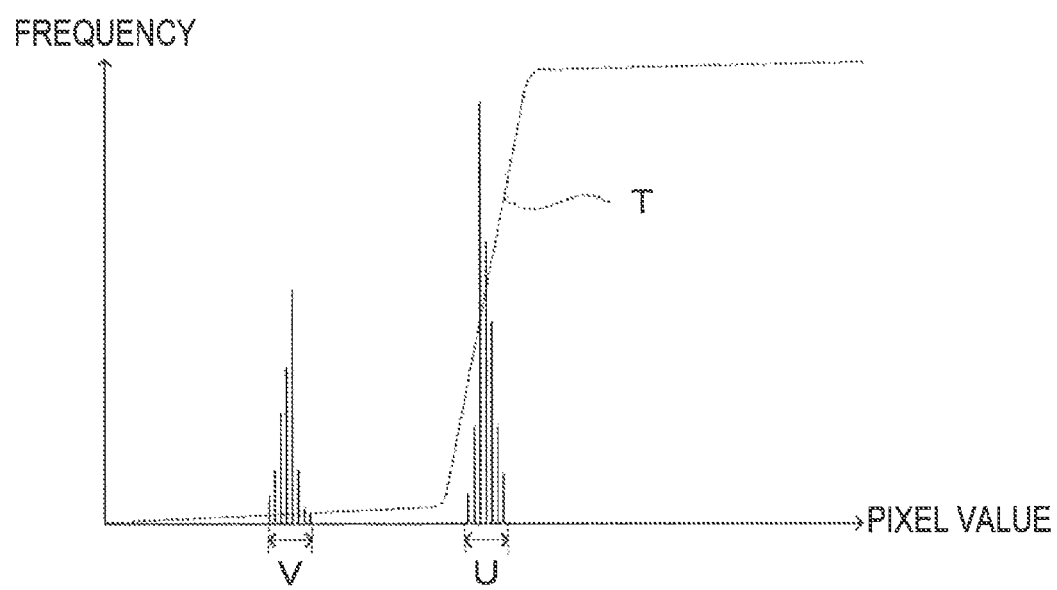
FIG. 25 is an explanatory view illustrating the relation between the tone curve deformed by the conventional method and the histogram of the substrate image.

Note that though the case of using the trigonometric function has been described as an example of the periodic function in the above embodiment, the tone curve may be created based on, for example, a function in a saw-tooth wave shape as illustrated in FIG. 17. Also in this case, an image with a high contrast can be obtained by appropriately setting the phase and the period.

Figure 12:
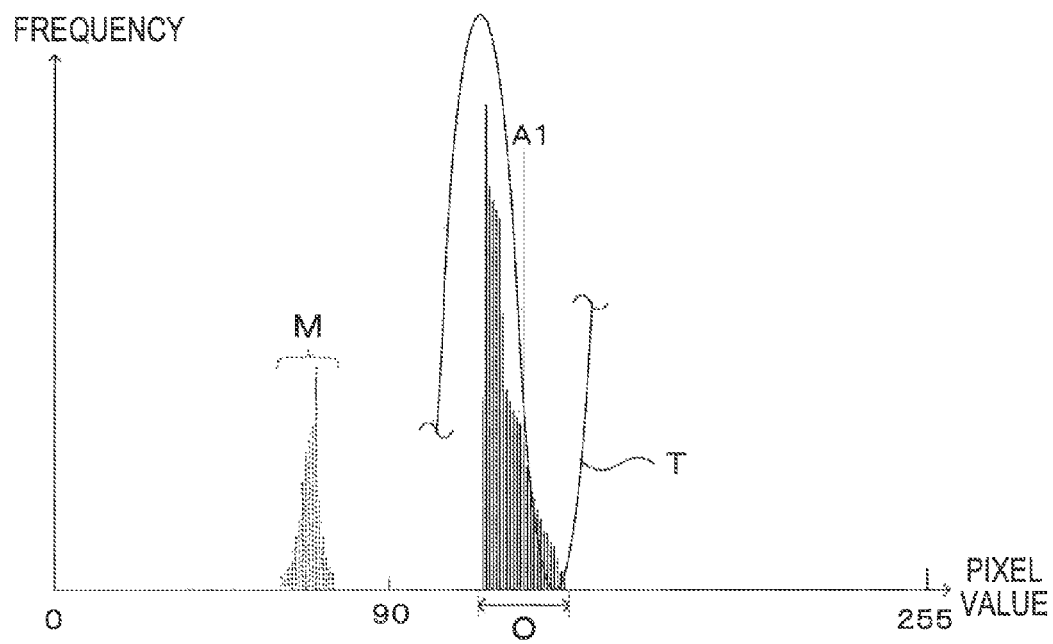
FIG. 12 is an explanatory view illustrating the relation between the tone curve according to the image processing of this embodiment and the histogram of the substrate image.

Note that when picking up an image of the wafer W, for example, being semiconductor, the pixel values corresponding to light from the illumination device 132 appear on the histogram as background information M as illustrated, for example, by broken lines in FIG. 12. Further, the illuminance of the illumination illuminating the wafer W by the illumination device 132 is adjusted so that the pixel value originating from a defect takes the pixel value not to overlap the background information M. Therefore, the tone curve may be created by subtracting the background information M from the total sum F of the frequencies of all pixel values. In this case, for example, assuming that the background information M exists in the region where the pixel value is equal to or lower than 90, it is possible to subtract the background information M from the total sum F by setting the value of i, which is 0 to 255 in Expression (2) for the whole, to 90 to 255. This enables performance of image processing with a higher accuracy.

EXAMPLES

As examples, the image processing apparatus 150 according to this embodiment was used to perform processing on substrate images. The substrate image before the image processing and the substrate image after the image processing are shown in each of FIG. 18 to FIG. 22. As the imaging device 130, an 8-bit CCD camera was used.

FIG. 18 shows the substrate images of the wafer W on which the defect of "wind ripple" occurred. The image after the image processing in FIG. 18 was obtained by using the tone curve having the value of the phase A set to "209" and the value of the period B set to "10." As shown in FIG. 18, though the defect was hardly confirmed in the state before the image processing, the contrast of the image is emphasized by performing the image processing of the present invention so that the occurrence of the defect at the peripheral portion of the wafer W can be clearly confirmed.

FIG. 19, FIG. 20, FIG. 21, and FIG. 22 show the substrate images of the wafers W on which the defects of "comet," "striation," "center mode," and "hot spot" occurred respectively. The images after the image processing in FIG. 19 to FIG. 22 have the values of the phase A set to "209," "186," "134," "119" and the value of the period B set to "10." It was confirmed from the results of the image processing shown in FIG. 19 to FIG. 22 that an image with a high contrast can be obtained in any case by performing the image processing of the present invention.

A preferred embodiments of the present invention has been described above with reference to the accompanying drawings, but the present invention is not limited to the embodiment. It should be understood that various changes and modifications are readily apparent to those skilled in the art within the scope of the spirit as set forth in claims, and those should also be covered by the technical scope of the present invention. The present invention is not limited to the embodiment and can take various aspects. The present invention is also applicable to the case where the substrate is substrates other than the wafer, such as an FPD (Flat Panel Display), a mask reticle for a photomask, and the like.

The present invention is useful in performing treatment on a substrate such as a semiconductor wafer.

What is claimed is:

1. An image processing method of picking up an image of a substrate and converting pixel values of the picked-up substrate image, comprising the steps of:
    making the pixel values of the picked-up substrate image into a histogram;
    creating a tone curve composed of a periodic function of a predetermined amplitude and a predetermined period based on a distribution of the pixel values in the histogram; and
    converting the pixel values of the picked-up substrate image using the tone curve.

2. The image processing method as set forth in claim 1, wherein the periodic function is a trigonometric function.

3. The image processing method as set forth in claim 2, wherein the trigonometric function is obtained by an expression expressed by $$Y=\{(2^C/2)-N\}\times[\sin\{(X-A)/B\}+1]$$

where Y: a pixel value after conversion
C: a number of bits of the substrate image
N: a positive constant equal to or larger than ½
X: a pixel value of the picked-up substrate image
A: a phase
B: a period.

4. The image processing method as set forth in claim 3, wherein A in the trigonometric function is a mode value of the pixel values in the histogram.

5. The image processing method as set forth in claim 1, wherein a shape of the tone curve is a saw-tooth wave shape, and the saw-tooth wave is the periodic function.

6. The image processing method as set forth in claim 1, wherein the periodic function is made by combining a plurality of trigonometric functions.

7. The image processing method as set forth in claim 6, wherein each of the plurality of trigonometric functions is obtained for each of a plurality of peaks of the pixel values existing in the histogram, and has a different period or phase.

8. A non-transitory computer-readable recording medium having a program recorded thereon for causing a computer to perform an image processing method of picking up an image of a substrate and converting pixel values of the picked-up substrate image,
    said image processing method comprising:
    making the pixel values of the picked-up substrate image into a histogram;
    creating a tone curve composed of a periodic function of a predetermined amplitude and a predetermined period based on a distribution of the pixel values in the histogram; and
    converting the pixel values of the picked-up substrate image using the tone curve.

9. An image processing apparatus converting pixel values of a substrate image picked up by an imaging device, comprising:
    a calculation part making pixel values of the picked-up substrate image into a histogram;
    an arithmetic part creating a tone curve composed of a periodic function of a predetermined amplitude and a predetermined period based on a distribution of the pixel values in the histogram; and
    a conversion part converting the pixel values of the picked-up substrate image using the tone curve.

10. The image processing apparatus as set forth in claim 9, wherein the periodic function is a trigonometric function.

11. The image processing apparatus as set forth in claim 10, wherein the trigonometric function is obtained by an expression expressed by $$Y=\{(2^C/2)-N\}\times[\sin\{(X-A)/B\}+1]$$

where Y: a pixel value after conversion
C: a number of bits of the substrate image
N: a positive constant equal to or larger than ½
X: a pixel value of the picked-up substrate image
A: a phase
B: a period.

12. The image processing apparatus as set forth in claim 11, wherein A in the trigonometric function is a mode value of the pixel values in the histogram.

13. The image processing apparatus as set forth in claim 9, wherein a shape of the tone curve is a saw-tooth wave shape, and the saw-tooth wave is the periodic function.

14. The image processing apparatus as set forth in claim 10, wherein the periodic function is made by combining a plurality of trigonometric functions.

15. The image processing apparatus as set forth in claim 14, wherein each of the plurality of trigonometric functions is obtained correspondingly to each of a plurality of peaks of the pixel values existing in the histogram.

16. The image processing apparatus as set forth in claim 10, further comprising:
    an image display apparatus displaying an image having the pixel values converted in said conversion part.

* * * * *